(12) United States Patent
Bruder

(10) Patent No.: US 7,634,044 B2
(45) Date of Patent: Dec. 15, 2009

(54) METHOD FOR GENERATING CARDIAC CT REPRESENTATIONS WITH APPLICATION OF A CONTRAST MEDIUM, AND MULTI-TUBE CT SYSTEM FOR CARRYING OUT THIS METHOD

(75) Inventor: Herbert Bruder, Höchstadt (DE)

(73) Assignee: Siemens Aktiengesellschaft, Munich (DE)

( * ) Notice: Subject to any disclaimer, the term of this patent is extended or adjusted under 35 U.S.C. 154(b) by 461 days.

(21) Appl. No.: 11/655,174

(22) Filed: Jan. 19, 2007

(65) Prior Publication Data
US 2007/0183561 A1 Aug. 9, 2007

(30) Foreign Application Priority Data
Jan. 20, 2006 (DE) .................. 10 2006 002 895

(51) Int. Cl.
G01N 23/083 (2006.01)
(52) U.S. Cl. .................. 378/9; 378/4; 378/98.12; 382/128; 600/431
(58) Field of Classification Search .................. 378/4, 378/5, 8, 9, 16, 98.9, 98.11, 98.12; 382/128–131; 600/425, 431
See application file for complete search history.

(56) References Cited

U.S. PATENT DOCUMENTS

| | | | | |
|---|---|---|---|---|
| 6,473,634 B1 * | 10/2002 | Barni | ............ | 600/425 |
| 2005/0111754 A1 * | 5/2005 | Cakir et al. | .......... | 382/284 |
| 2005/0163283 A1 | 7/2005 | Bruder et al. | | |
| 2005/0185829 A1 * | 8/2005 | Heismann | ............ | 382/128 |
| 2006/0159220 A1 * | 7/2006 | Heuscher | .......... | 378/9 |
| 2006/0247518 A1 | 11/2006 | Boing et al. | | |
| 2008/0226017 A1 * | 9/2008 | Altman et al. | .......... | 378/4 |

FOREIGN PATENT DOCUMENTS

DE  10 2004 004 295 A1  8/2005
DE  10 2005 018 066 A1  10/2006

OTHER PUBLICATIONS

Ohnesorge et al., Somation Sessions 17, Dec. 2005, Siemens AG.*
Manzke, Cardiac Cone Beam CT, Sep. 2004, Doctoral Dissertation, Division of Imaging Science, King's College London.*
Hoffman et al., Noninvasive Coronary Angiography with 16-Detector Row CT: Effect of Heart Rate, 2004, Radiology, vol. 234, pp. 86-97.*

* cited by examiner

Primary Examiner—Edward J Glick
Assistant Examiner—John M Corbett
(74) Attorney, Agent, or Firm—Harness, Dickey & Pierce, P.L.C.

(57) ABSTRACT

A method is disclosed for generating cardiac CT representations of a beating heart of a patient with the aid of a multi-tube CT system with application of a contrast medium. In at least one embodiment, the method includes carrying out a first CT scan with the multi-tube CT system, wherein at least one tube generates an X-ray spectrum, and reconstructing at least one CT representation of the same cardiac phase with a first temporal resolution; subsequently carrying out a second CT scan with the multi-tube CT system, wherein at least two angularly offset tubes generate different X-ray spectra; reconstructing at least one CT representation of the same cardiac phase per X-ray spectrum with a second temporal resolution; and generating a combined CT representation from results of the first and of the second scan.

21 Claims, 2 Drawing Sheets

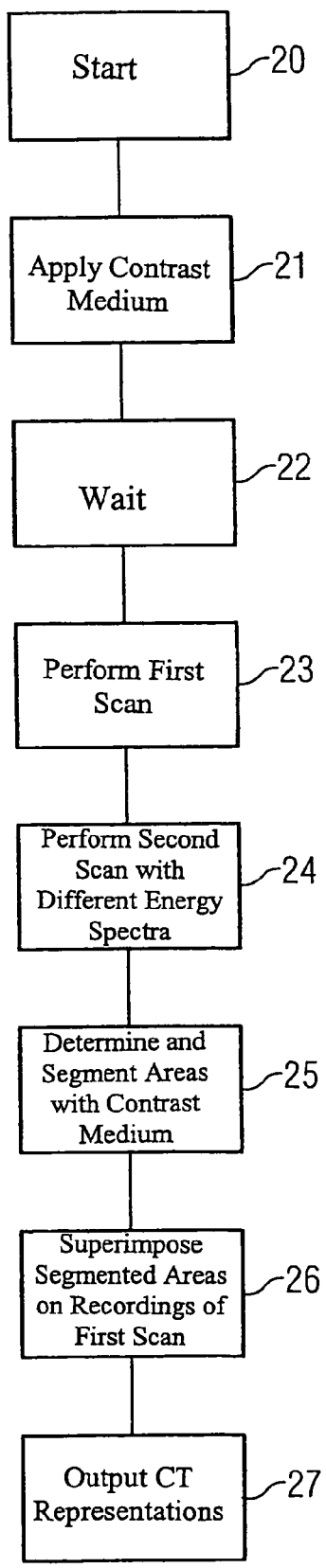

METHOD FOR GENERATING CARDIAC CT REPRESENTATIONS WITH APPLICATION OF A CONTRAST MEDIUM, AND MULTI-TUBE CT SYSTEM FOR CARRYING OUT THIS METHOD

PRIORITY STATEMENT

The present application hereby claims priority under 35 U.S.C. § 119 on German patent application number DE 10 2006 002 895.3 filed Jan. 20, 2006, the entire contents of which are hereby incorporated herein by reference.

FIELD

Embodiments of the invention generally relate to a method for generating cardiac CT representations of a beating heart of a patient with the aid of a multi-tube CT system with application of a contrast medium. In addition, embodiments of the invention may generally relate to a multi-tube CT system having at least two radiation sources and a contrast medium application device. For example, they may relate to one by which a patient can be scanned with application of contrast medium, wherein each radiation source can generate different X-ray spectra for the scanning and a control and computing unit is connected which has at least one memory for programs and data, and a reconstruction of tomographic representations is carried out with the stored programs and projection data.

BACKGROUND

Methods and multi-tube CT systems are generally known. For example, reference is made to the patent application, not previously published, having the official file reference DE 10 2005 018 066.3. Such methods and CT systems can be used, for example, for measuring the blood flow through the cardiac wall by determining the wall perfusion after an application of contrast medium. In this process, a relatively limited area of the heart is continuously scanned due to the small extent in the direction of the system axis of the detectors currently available and the accumulated concentration in the cardiac wall tissue is observed. A problem here is the relatively high dose rate applied to the patient due to the prolonged scan. This strain could be reduced. In addition, it would also be desirable if it were possible to enlarge the cardiac region observed.

Reference is also made to patent application 10 2004 004 295 A1, which discloses a method for generating CT representations with the aid of a two-tube CT system with application of a contrast medium, wherein, during the CT scan, the two X-ray tubes arranged with offset angles generate two X-ray spectra with different spectral distribution and a subtraction image is generated from the CT images reconstructed separately for each X-ray spectrum.

SUMMARY

In at least one embodiment of the invention, a method and a CT system are disclosed which supply results for the wall perfusion of the heart by using a lower X-ray dose.

The inventor has recognized, in at least one embodiment, that the contrast resolution of cardiac CT representations with application of a contrast medium. can be enhanced by using spectral CT data of a multi-tube system.

Accordingly, the inventor proposes, in at least one embodiment, to improve the known method for generating cardiac CT representations of a beating heart of a patient with the aid of a multi-tube CT system with application of a contrast medium in such a way that, instead of a prolonged continuous scan of the heart region, the following steps are performed:

carrying out a first CT scan with the multi-tube CT system wherein at least one tube generates an X-ray spectrum, and reconstructing at least one CT representation of the same cardiac phase with a first temporal resolution, subsequently carrying out a second CT scan with the multi-tube CT system, wherein at least two angularly offset tubes generate different X-ray spectra, reconstructing at least one CT representation of the same cardiac phase per X-ray spectrum with a second temporal resolution, and generating a combined CT representation, from results of the first and of the second scan.

By carrying out two scans offset in time, the last scan being carried out with different energy spectra as a result of which even slight concentrations of contrast medium can be represented particularly well, regions with pathologically reduced wall perfusion can be located particularly easily.

For this purpose, it may be particularly advantageous if the contrast medium is applied before the first CT scan. The time interval can be dimensioned in such a manner that the greatest concentration in the large cardiac vessels is already achieved at the time of the first scan. The second scan with different spectra occurs correspondingly later, the concentration of contrast medium being distinctly reduced in the large blood vessels but—in the normal case—the contrast medium having been absorbed in the cardiac wall and being verifiable in the small blood vessels.

However, it is also possible to carry out the first scan without contrast medium in order to obtain an optimum representation of the cardiac tissue without the influence of adjacent, greatly increased absorptions and to carry out the application of the contrast medium for the second CT scan. When the timing of application and scan is correspondingly matched, regions with disturbed or excessive perfusion can then be detected.

An improvement of the method according to at least one embodiment of the invention can be achieved if, in the first CT scan, already at least two angularly offset X-ray tubes are used which generate the same X-ray spectrum and the reconstruction is carried out with data from both X-ray tubes. In the ideal case, this allows twice as high a temporal resolution of the CT representation to be produced. As a result this provides CT representations with much less motion blurring. The first temporal resolution of the first CT scan is thus higher than the temporal resolution of the second CT scan with $\Delta T_1 < \Delta T_2$.

The representation generated by the scans offset in time can be combined in such a manner, for example, that voxels or pixels with particular HU value differences of HU value ratios from the second scan are emphasized, possibly colored, and are overlaid with the image of the first scan.

However, with the CT representations of the second scan, a segmentation can be carried out on the basis of different HU values in dependence on the X-ray spectrum used, the segmentation criterion used being, for example, the quotient $HU(S_1)/HU(S_2)$ or the difference $|HU(S_1)-HU(S_2)|$ of the respective HU values ($HU(S_1)$, $HU(S_2)$) of identical pixels or voxels from the different spectra ($S_1, S_2$). The areas of the CT representation thus segmented can then be used for identifying pathological or at least suspected areas of the heart by a superposition with the image of the first—possibly sharper—scan. In the combined CT representation, the areas with contrast medium accumulation can also be represented colored in such a manner that, by using different colors, the color itself represents the degree of pathological change in the cardiac wall.

The different X-ray spectra can be produced, for example, by different filtering of the radiation and/or different tube voltage for generating the X-radiation. In this context it is advantageous to match the X-ray spectra used and the contrast medium used to one another in such a manner that the greatest possible difference in the absorption characteristic of the contrast medium occurs at the different spectra selected. This facilitates the recognition of slight contrast medium concentrations when comparing the CT values from the different spectra.

To provide an improved representation and better discrimination of large vessels and tissues with accumulated contrast medium, areas with contrast medium filling from the first CT scan can be represented with a different color than areas with contrast medium filling from the second scan.

To improve or even optimize the method according to at least one embodiment of the invention, it is also proposed that the time interval between the first and the second CT scan is selected in such a manner that an accumulation is achieved in a healthy cardiac wall but is not yet achieved in an infarct tissue.

According to a further proposal of at least one embodiment, in addition to a scan with different X-ray spectra, further CT scans with in each case at least two different X-ray spectra can be carried out and further combined representations can be generated from results of the first CT scan with one energy spectrum and the further CT scans with different spectra. In this manner, the development of the accumulation of contrast medium with time in the cardiac tissue observed can be represented.

In a particularly advantageous variant, the method according to at least one embodiment of the invention can be carried out in conjunction with spiral scans. This makes it possible to observe the entire cardiac volume, even without wide multi-row detectors.

According to a further variant of at least one embodiment of the invention, it is proposed that, between the first CT scan and the CT scans with simultaneously used different X-ray spectra with a reduced dose, so-called pilot scans are carried out by which the contrast medium content in large blood vessels is measured in a coarse resolution. Such pilot scans can be performed with much lower radiation dose rate since they are not used for precise image representation. For this purpose, it is either possible to reduce the radiation dose rate of the X-ray tube or there is the possibility of greatly restricting the radiation cone for the pilot scan, for example to such an extent that only one detector row is illuminated. This is sufficient for detecting the change in contrast medium concentration in the area of large blood vessels of interest without having to generate a high-resolution image. Such pilot scans can also take place intermittently at time intervals which can also be adapted, for example, in accordance with the measured change in concentration of the contrast medium.

The method represented, in at least one embodiment, is not only suitable for representing the perfusion characteristics of cardiac tissue but, by using different X-ray spectra, another organ can be scanned instead of the heart, preferably the brain and the variation with time of the contrast medium concentration can be measured at at least two times in order to determine, for example the regions affected by a stroke.

In accordance with at least one embodiment of the method described above, the inventor also proposes a multi-tube CT system comprising at least two radiation sources and a contrast medium application device by means of which a patient can be scanned with application of contrast medium, wherein each radiation source can generate different X-ray spectra for the scanning and a control and computing unit is connected which has at least one memory for programs and data, and a reconstruction of tomographic representations is carried out with the stored programs and projection data, wherein computer programs or program modules are stored which, in operation, carry out the method steps of the method described above.

BRIEF DESCRIPTION OF THE DRAWINGS

In the text which follows, the invention will be explained in greater detail with the aid of figures with reference to an example embodiment, only the features necessary for understanding the invention being shown. The following reference symbols were used for the description: 1: CT system; 2: first X-ray system axis; 10: control and computing unit; 11: memory; 12: contrast medium pump; 13: ECG line; 14: control and data line; 15: contrast medium line; 20: start of the scan; 21: application of the contrast medium; 22: cardiac CT scan; 23: defined pause; 24: scan with different energy spectra; 25: comparison of the CT recordings; 26: superposition of the CT recording; 27: output of the revised CT representations; $Prg_1$-$Prg_n$: computer programs; $Prg_x$: program module; in detail:

FIG. 2 shows a method scheme of an example embodiment of the method according to the invention.

DETAILED DESCRIPTION OF THE EXAMPLE EMBODIMENTS

Figure 1:
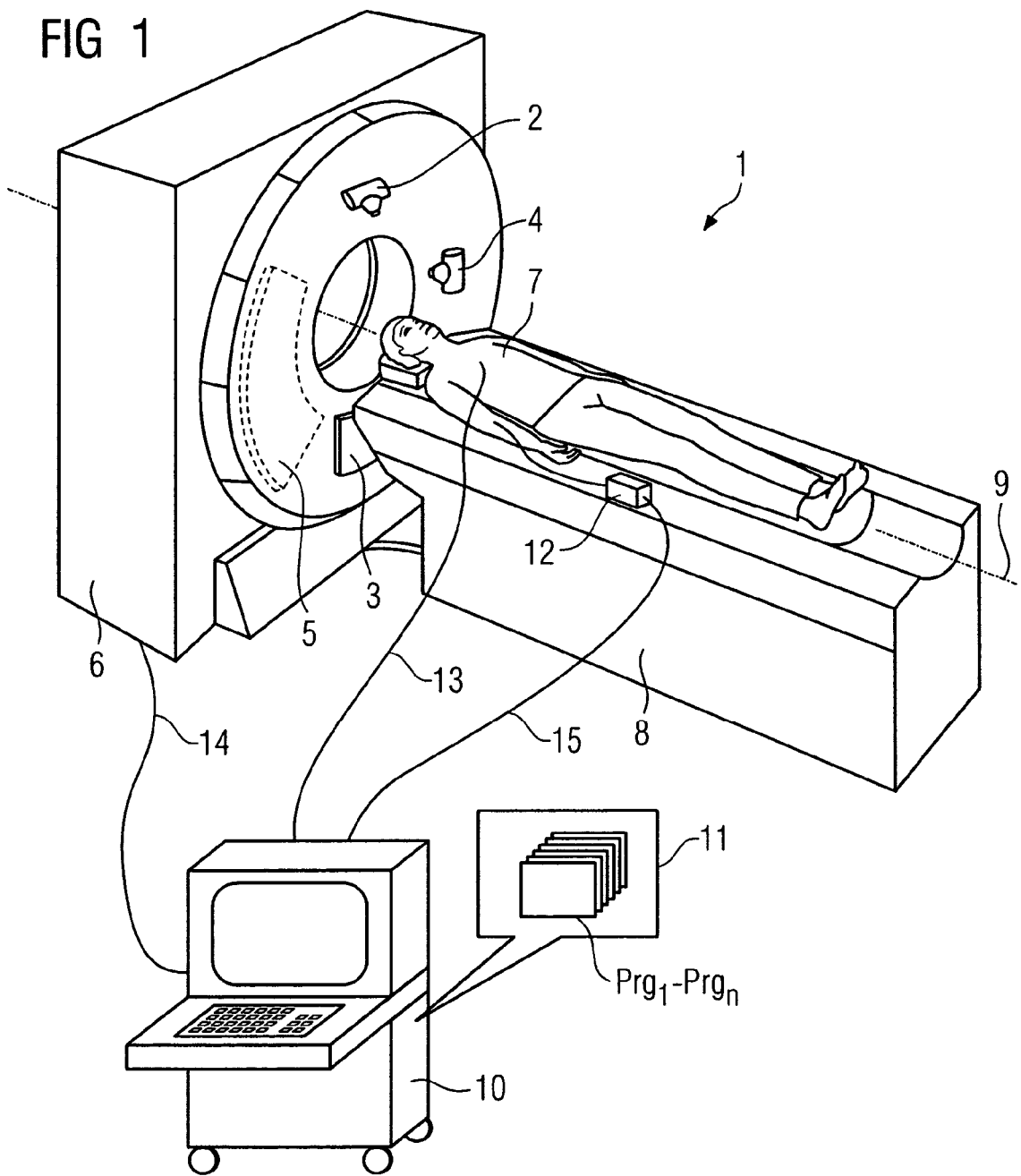
FIG. 1 shows a CT system with contrast medium application device.

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

FIG. 1 shows a CT system suitable for carrying out the method according to an embodiment of the invention. Such a CT system 1 has a first X-ray tube 2 with an oppositely located detector 3 and a second X-ray tube 4 with a further oppositely located detector 5. Both focus/detector systems 2, 3 and 4, 5 are arranged in a gantry housing 6 on a gantry rotating around a system axis 9 but not shown visibly here. The patient 7 is located on a longitudinally displaceable patient couch 8 which is pushed continuously or incrementally through an opening in the gantry housing 6 for scanning the patient 7 during the rotation of the focus/detector systems. As a result, the patient 7 is scanned spirally or several times circularly.

To control the CT system 1, a control and computing unit 10 is used which has in its memory 11 computer programs and program modules $Prg_x$ which, in operation, are loaded and processed as required. The control itself and the reading out of detector output data are done via the control and data line 14 which connects the control and computing unit 10 to the gantry housing 6. Contrast medium is applied with the aid of a contrast medium pump 12, also controlled by the control and computing unit 10 via the line 15, which venously applies the contrast medium in a predetermined manner. In addition, the cardiac potentials are derived via an ECG line 13 for the cardiac scan in conjunction with which the control and computing unit 10 takes over the function of an ECG device here, too, and can generate in this manner a collection of detector data matching cardiac phases, which are used for the reconstruction of cardiac CT recording in a manner known per se.

FIG. 2 diagrammatically shows a preferred flowchart of the method according to an embodiment of the invention. Accordingly, after the start 20 in the first method step 21 contrast medium is injected into the patient 7 with a defined flow rate, which may be varied over time, at a particular time. Following this, a cardiac CT scan is carried out in step 22 with the two tube/detector systems 2, 3, 4 and 5 using a uniform energy spectrum, adapted in time to the optimum contrast medium concentration to be expected in the large cardiac vessels, wherein the measured detector data of both detectors are collected for the same cardiac phase by simultaneously recording ECG signals and are used for the reconstruction. By using the two tube/detector systems 2, 3, 4 and 5, arranged angularly offset by 90°, about twice as high a temporal resolution is possible compared with a one-tube/detector system so that recordings with greatly reduced motion blurring can be reconstructed. The large blood vessels well filled with contrast medium can be clearly recognized in these recordings. Scanning is performed by a spiral scan so that the entire heart is also represented with narrow detectors.

In method step 23, the system waits for a predetermined time without scanning or, at the most, with a low-dosage pilot scan. In this time, a different acceleration voltage can be selected and/or another radiation filter can be inserted into the beam path either in both tube/detector systems 2, 3, 4 and 5 or in only one tube/detector system so that two different energy spectra can be utilized during the subsequent scanning.

After the predetermined time has elapsed or a predetermined contrast medium concentration has been reached, scanning begins with different energy spectra in method step 24. Since, due to the different absorption characteristic, the detector data of each tube/detector system 2, 3 and 4, 5 must be observed separately and separate reconstructions must be carried out, the temporal resolution of these CT recordings thus reconstructed is poorer.

In method step 25, the CT recordings of the second scan are now compared with one another pixel by pixel or voxel by voxel and areas are determined which, due to their different CT values, allow the presence of contrast medium to be inferred. These areas are segmented, wherein the large blood vessels recognized in the first scan can be advantageously excluded from this. Following this, the segmented areas from the second scan are superimposed on the high-resolution CT recordings of the first scan in step 26, wherein the segmented areas can be represented in color. In method step 27, the CT representations thus edited are output on a console where the observer sees the regions of the cardiac tissue with sufficient perfusion, which are emphasized by being identified in color, as displayed in color.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating cardiac Computed Tomography (CT) representations of a beating heart of a patient with the aid of a multi-tube CT system with application of a contrast medium, the method comprising:
    carrying out a first CT scan with the multi-tube CT system, wherein at least one tube generates an X-ray spectrum, and reconstructing at least one CT representation of a cardiac phase with a first temporal resolution;
    subsequently carrying out a second CT scan with the multi-tube CT system, wherein at least two angularly offset tubes generate different X-ray spectra;
    reconstructing at least one CT representation of the same cardiac phase per X-ray spectrum with a second temporal resolution; and
    generating a combined CT representation from results of the first and of the second scan.

2. The method as claimed in the preceding patent claim 1, wherein the contrast medium is applied before the first CT scan.

3. The method as claimed in claim 2, wherein the contrast medium is applied for the second CT scan.

4. The method as claimed in claim 2, wherein the contrast medium is applied intravenously.

5. The method as claimed in claim 1, wherein the contrast medium is applied for the second CT scan.

6. The method as claimed in claim 1, wherein the contrast medium is applied intravenously.

7. The method as claimed in claim 1, wherein in the first CT scan, at least two angularly offset X-ray tubes generate the same X-ray spectrum and the reconstruction is carried out with data from both X-ray tubes.

8. The method as claimed in claim 7, wherein the first temporal resolution is higher than the second temporal resolution.

9. The method as claimed in claim 1, wherein with the CT representations of the second scan, a segmentation is carried out on the basis of different Hounsfield unit (HU) values in dependence on the X-ray spectrum used.

10. The method as claimed in claim 9, wherein the quotient $HU(S_1)/HU(S_2)$ of the respective HU values ($HU(S_1)$, $HU(S_2)$) of identical pixels or voxels from the different X-ray spectra ($S_1$, $S_2$) is used as the segmentation criterion.

11. The method as claimed in claim 9, wherein the difference $|HU(S_1)-HU(S_2)|$ of the respective HU values ($HU(S_1)$, $HU(S_2)$) of identical pixels or voxels from the different X-ray spectra ($S_1$, $S_2$) is used as the segmentation criterion.

12. The method as claimed in claim 1, wherein the at least two different X-ray spectra are produced by at least one of a different filtering of the radiation and a different tube voltage for generating the X-radiation.

13. The method as claimed in claim 1, wherein in the combined CT representation, areas with contrast medium accumulation are represented in color.

14. The method as claimed in claim 13, wherein areas with contrast medium filling from the first CT scan are represented with a different color than areas with contrast medium filling from the second scan.

15. The method as claimed in claim 1, wherein the time interval between the first and the second CT scan is selected in such a manner that a contrast medium accumulation is achieved in a healthy cardiac wall but is not yet achieved in an infarct tissue.

16. The method as claimed in claim 1, wherein further CT scans with in each case two different X-ray spectra are carried out and further combined representations are generated from results of the first CT scan with one X-ray spectrum and the further CT scans with different X-ray spectra.

17. The method as claimed in claim 1, wherein the CT scans are carried out as spiral scans.

18. The method as claimed in claim 1, wherein, between the first CT scan and the CT scans with simultaneously used different X-ray spectra with a reduced dose, pilot scans are carried out by which the contrast medium content in large blood vessels is measured in a coarse resolution.

19. The method as claimed in claim 18, wherein for the pilot scans, the radiation cone is restricted to one detector row.

20. A multi-tube Computed Tomography (CT) system, comprising:
   at least two radiation sources;
   a contrast medium application device, to scan a patient with application of contrast medium, wherein each radiation source generate different X-ray spectra for the scanning; and
   a control and computing unit, including at least one memory for programs and data, wherein a reconstruction of tomographic representations is carried out with the stored programs and projection data, and wherein at least one program modules is stored which, in operation, is adapted to execute the following,
      reconstructing at least one CT representation of a cardiac phase with a first temporal resolution after a first CT scan is carried out with the multi-tube CT system, wherein at least one tube generates an X-ray spectrum,
      reconstructing at least one CT representation of the same cardiac phase per X-ray spectrum with a second temporal resolution after a second CT scan is carried out with the multi-tube CT system, wherein at least two angularly offset tubes generate different X-ray spectra; and
      generating a combined CT representation from results of the first and of the second scan.

21. A multi-tube Computed Tomography (CT) system, comprising:
   means for carrying out a first CT scan;
   means for reconstructing at least one CT representation of a cardiac phase with a first temporal resolution;
   means for subsequently carrying out a second CT scan, wherein at least two angularly offset tubes generate different X-ray spectra;
   means for reconstructing at least one CT representation of the same cardiac phase per X-ray spectrum with a second temporal resolution; and
   means for generating a combined CT representation from results of the first and of the second scan.

* * * * *